United States Patent [19]

Yu et al.

[11] Patent Number: 5,776,771
[45] Date of Patent: Jul. 7, 1998

[54] KANAMYCIN RESISTANCE GENE DERIVED FROM MICROORGANISMS OF THE GENUS RHODOCOCCUS

[75] Inventors: Fujio Yu; Mami Kato, both of Yokohama, Japan

[73] Assignee: Nitto Chemical Industry Co., Ltd., Tokyo, Japan

[21] Appl. No.: 510,878

[22] Filed: Aug. 3, 1995

[30] Foreign Application Priority Data

Aug. 4, 1994 [JP] Japan .................................. 6-201582

[51] Int. Cl.⁶ .......................... C12N 1/21; C12N 15/31; C12N 15/70; C12N 15/74
[52] U.S. Cl. .................. 435/320.1; 435/252.3; 435/252.33; 536/23.2; 536/23.7
[58] Field of Search ........................ 435/252.3, 252.33, 435/320.1; 536/23.2, 23.7

[56] References Cited

U.S. PATENT DOCUMENTS

| 4,920,054 | 4/1990 | Kozlowski et al. | 435/252.31 |
|---|---|---|---|
| 5,246,857 | 9/1993 | Yu et al. | 435/320.1 |

FOREIGN PATENT DOCUMENTS 05 02476A2  9/1992  European Pat. Off.

OTHER PUBLICATIONS

Berg et al., *Proc. Nat. Acad. Sci, USA*, vol. 72, No. 9, pp. 3628–3632 (Sep. 1975).

Hashimoto et al., *Journal of General Microbiology*, vol. 138, pp. 1003–1010 (1992).

Dabbs et al., *PLASMID*, vol. 23, No. 3, pp. 242–247, (May 1990).

*Primary Examiner*—Johnny F. Railey, II
*Attorney, Agent, or Firm*—Birch, Stewart, Kolasch & Birch, LLP

[57] ABSTRACT

The present invention relates to a DNA derived from microorganisms of the genus Rhodococcus and conferring kanamycin resistance on hosts with a DNA sequence coding for the amino acid sequence of Sequence No. 1 or a polypeptide containing a partial sequence thereof. The kanamycin resistance gene of the present invention is useful to construct vectors for microorganisms of the genus Rhodococcus, particularly vectors for self-cloning of *Rhodococcus rhodochrous*.

12 Claims, 4 Drawing Sheets

5,776,771

KANAMYCIN RESISTANCE GENE DERIVED FROM MICROORGANISMS OF THE GENUS RHODOCOCCUS

FIELD OF THE INVENTION

The present invention relates to a gene derived from microorganisms of the genus Rhodococcus and conferring kanamycin resistance on bacteria, as well as a plasmid vector containing the same.

BACKGROUND OF THE INVENTION

Microorganisms belonging to the genus Rhodococcus are known as bacterial catalysts that hydrate or hydrolyze nitriles to the corresponding amides or acids (Japanese Patent Publication No. 4873/92 and Japanese Laid-Open Patent Publication Nos. 91189/87, 470/90 and 84198/90), and in particular, microorganisms belonging to the species *Rhodococcus rhodochrous* possess nitrile-hydrating activity of extremely high performance (Japanese Laid-Open Patent Publication No. 470/90).

Under such circumstances, one of the present inventors found cryptic plasmids in a certain strain of the species *Rhodococcus rhodochrous* and constructed hybrid plasmid vectors to develop a host-vector system of the genus Rhodococcus (Japanese Laid-Open Patent Publication Nos. 148685/92, 64589/93 and 68566/93).

For construction of a self-cloning system of higher safety, it is also necessary to develop maker genes derived from microorganisms of the genus Rhodococcus. However, only arsenious acid and cadmium resistance genes derived from microorganisms of the species *Rhodococcus rhodochrous* are known as such drug resistance genes (Plasmid 23, 242–247 (1990)).

SUMMARY OF THE INVENTION

With the aim of establishing a self-cloning system of the genus Rhodococcus, the present inventors extensively studied drug resistance genes derived from microorganisms of the genus Rhodococcus, in particular the species *Rhodococcus rhodochrous*, so that they found the kanamycin resistance gene of the present invention.

That is, the present invention relates to a DNA derived from microorganisms of the genus Rhodococcus and conferring kanamycin resistance on hosts with a DNA sequence coding for the amino acid sequence of Sequence No. 1 or a polypeptide containing a partial sequence thereof.

DETAILED DESCRIPTION OF THE INVENTION

Figure 1:
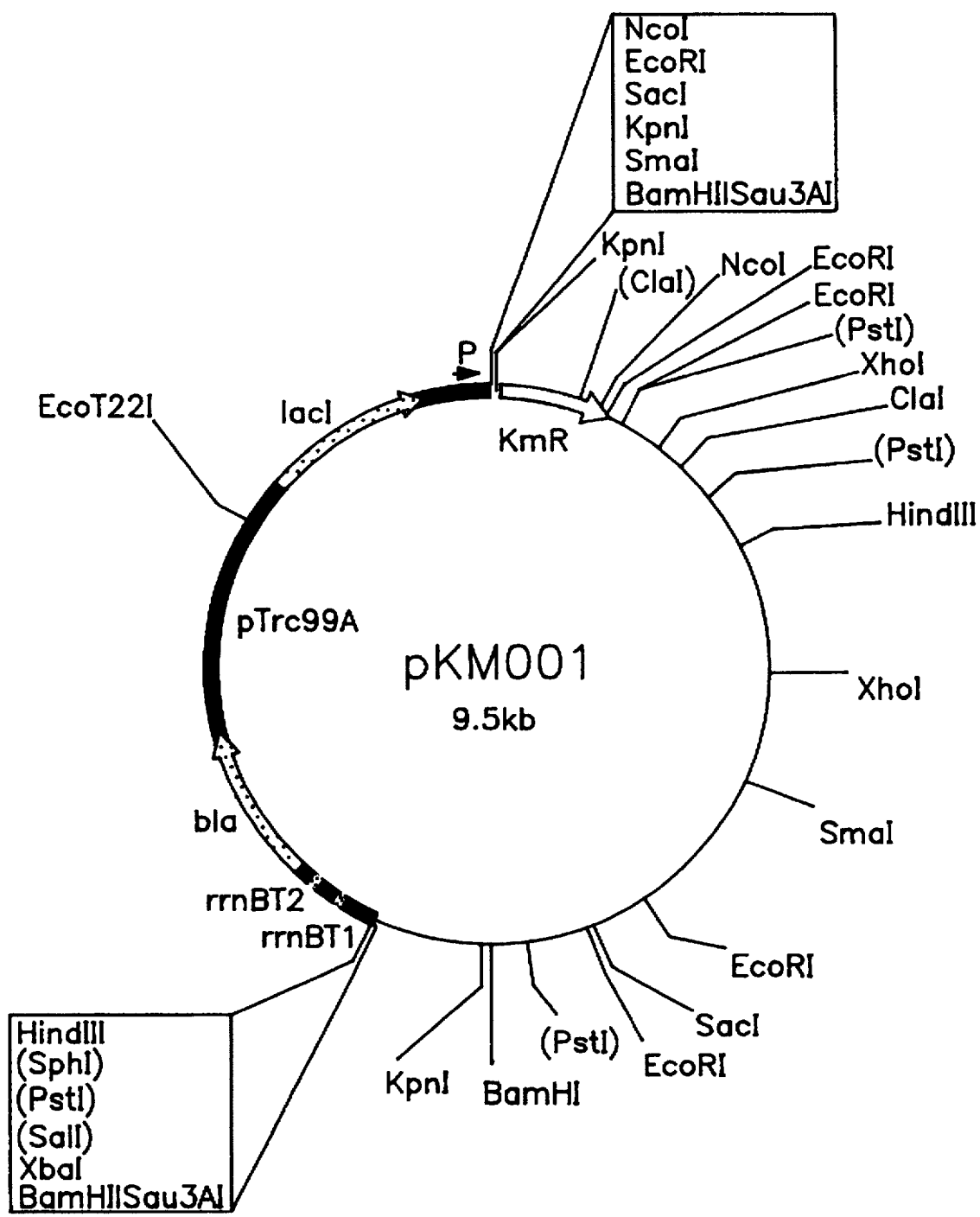
FIG. 1 shows a restriction enzyme map of plasmid pKM001.

As the DNA donor in the present invention, mention may be made of kanamycin mutant KM-02 (deposited as FERM BP-5137 with the National Institute of Bioscience and Human-Technology, Agency of Industrial Science and Technology, Japan) which was obtained by spontaneous mutation of *Rhodococcus rhodochrous* ATCC 12674.

As the vectors used in cloning in the present invention, mention may be made of plasmid vectors including but not limited to *E. coli* vectors such as pTrc99A, pUC18, etc. and phage vectors such as λgt11 etc. The host microorganisms include but are not limited to *E. coli* JM109, *E. coli* JM105, and *Rhodococcus rhodochrous* ATCC 12674.

Plasmids that provide plasmid vectors constructed of the kanamycin resistance gene of the invention with a region capable of replicating in microorganisms of the genus Rhodococcus include, but are not limited to, plasmids pRCO01, pRC002, pRC003 and pRC004. The plasmids pRCO01, pRC002, pRC003 and pRC004 are derived from *Rhodococcus rhodochrous* ATCC 4276, ATCC 14349, ATCC 14348 and IFO 3338, respectively, and these plasmids are described in the aforementioned Japanese Laid-Open Patent Publication Nos. 148685/92, 64589/93 and 68566/93, respectively.

The present kanamycin resistance gene derived from microorganisms of the genus Rhodococcus is useful to construct vectors for microorganisms of the genus Rhodococcus, particularly vectors for self-cloning of *Rhodococcus rhodochrous*.

EXAMPLES

The present invention is described in more detail with reference to the following examples, which however are not intended to limit the scope of the present invention.

Example 1

Cloning of Kanamycin Resistance Gene from Mutant KM-02 into *E. coli* JM109

(1) Preparation of genomic DNA from KM-02 and preparation of a DNA library

The KM-02 strain was cultured under shaking at 30° C. in 100 ml MY medium (0.5% polypeptone, 0.3% Bacto-yeast extract, 0.3% Bacto-malt extract) and genomic DNA was prepared from the bacteria according to the method by Saito and Miura (Biochim. Biophys. Acta 72, 619 (1963)). A part of the resulting DNA was partially digested with restriction enzyme Sau3AI and then inserted into a BamHI site of *E. coli* vector pTrc99A to give a recombinant DNA library.

(2) Preparation of transformants and selection of recombinant DNA

The recombinant library prepared in step (1) was used to transform *E. coli* JM109 by the calcium chloride method, and transformants with resistant to kanamycin were selected in the following manner.

The transformants obtained above were plated onto LB agar medium (1% Bacto-trypton, 0.5% Bacto-yeast extract, 0.5% NaCl, 1.5% agar) containing 40 µg/ml kanamycin hydrochloride and 1 mM IPTG (isopropyl-β-thiogalactoside) and incubated overnight at 37° C. The colonies occurring thereon were removed and applied onto the same agar medium, and their growth was confirmed.

A plasmid DNA was prepared from the thus obtained transformant according to the method by Birnboim and Doly (Nucleic Acid Res. 7, 1513–1523 (1979)) and designated pKM001. This plasmid was reintroduced into *E. coli*, and the resultant transformant with kanamycin resistance was designated JM109/pKM001 and deposited as FERM BP-5138 with the National Institute of Bioscience and Human-Technology, Agency of Industrial Science and Technology. IPTG was required for expression of Kanamycin resistance of *E. coli* JM109/pKM001.

(3) A restriction enzyme map of pKM001 and location of the kanamycin resistance gene A restriction enzyme map of plasmid pKM001 obtained in step (2) was prepared (FIG. 1). Thereafter, this plasmid pKM001 was used for preparing plasmids of a smaller DNA fragment. The target gene-containing region was identified by the presence or absence of the kanamycin resistance of transformants prepared in the same manner as in step (2). During this process, plasmid pKM002 (FIG. 2) was constructed.

(4) Nucleotide sequencing

The nucleotide sequence of the kanamycin resistance gene in plasmid pKM002 was determined by Fluorescence Sequencer ALF II produced by Pharmacia (Sequence No. 3).

Example 2

Preparation of Hybrid (*E. Coli*-Rhodococcus) Plasmid Vector Carrying the Kanamycin Resistance Gene Derived from *Rhodococcus rhodochrous*

A hybrid plasmid vector pK4, previously constructed by one of the present inventors by ligating Rhodococcus-derived plasmid pRC004 with *E. coli* vector pHSG299 and deposited as FERM BP-3731 with the National Institute of Bioscience and Human-Technology, Agency of Industrial Science and Technology (Japanese Laid-Open Patent Publication Nos. 64589/93 and 68566/93), was used for preparing a 3.1 kb HindIII fragment containing the whole of pRC004 and a part of pHSG299, and the resulting fragment was ligated with the plasmid pKM002.

Figure 2A:
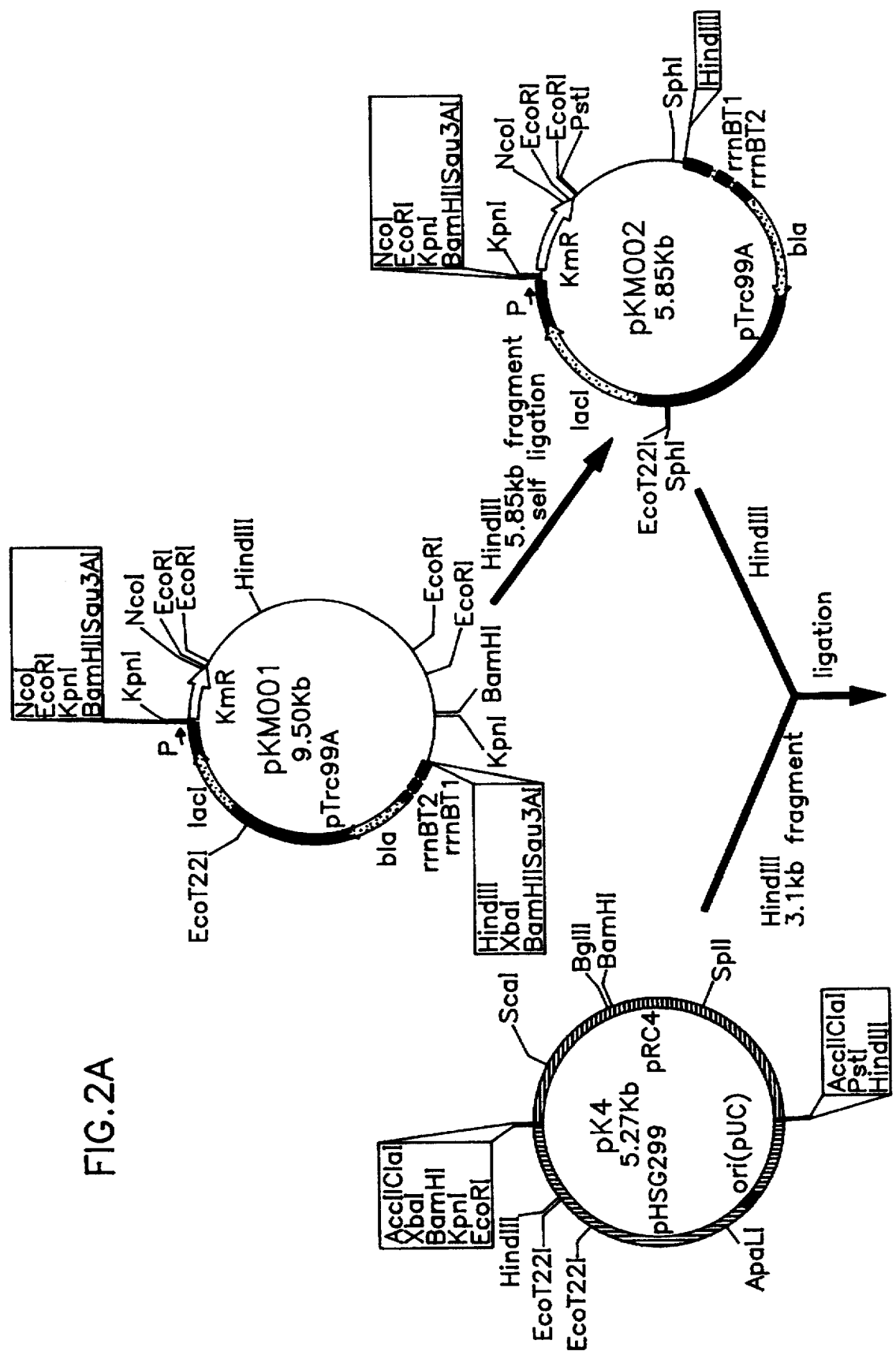
FIG. 2 shows the construction of plasmid pKM002, pKM003 and pKM004.
Figure 2B:
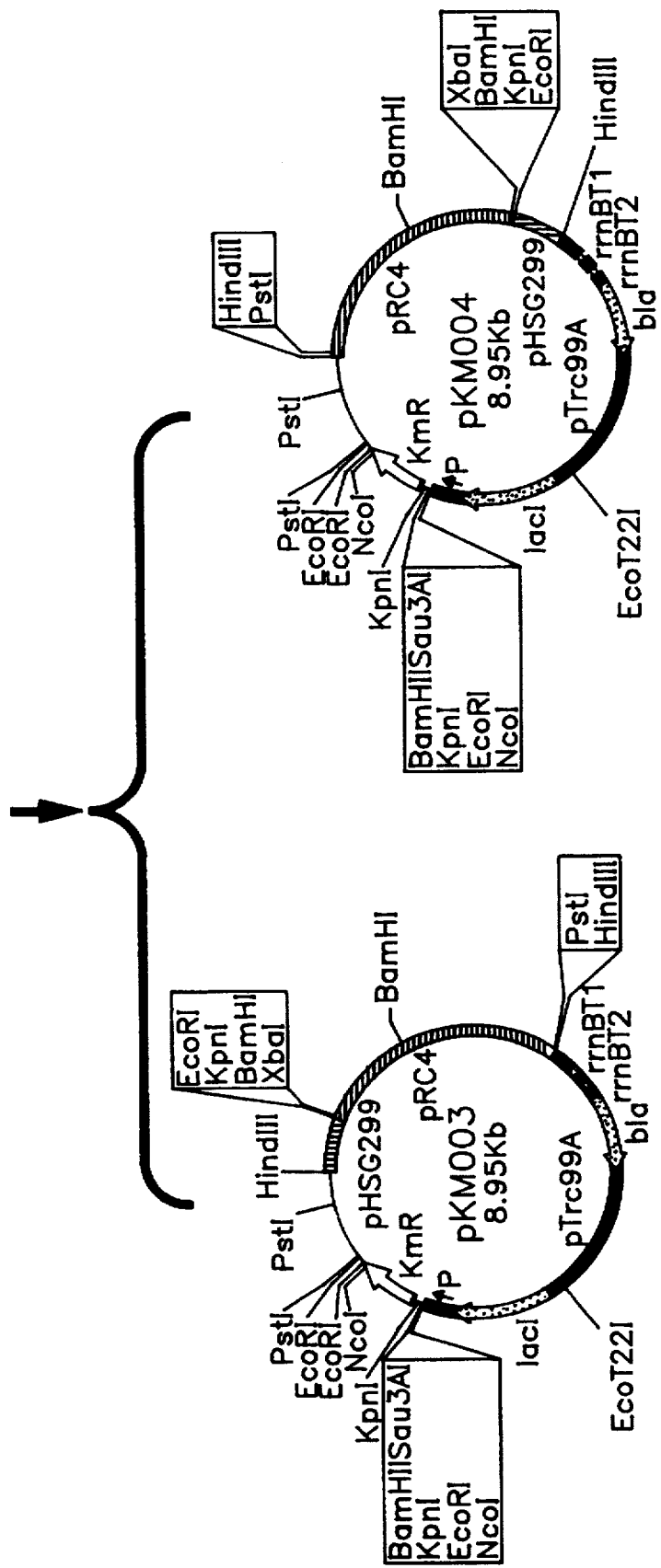

As a result, two plasmids carrying the insert in the opposite direction were obtained and designated pKM003 and pKM004 respectively (FIG. 2). These plasmids replicate in both the genus Rhodococcus and *E. coli*. *Rhodococcus rhodochrous* ATCC 12674 was transformed with these plasmids by electroporation, whereby a transformant capable of growing in MY medium containing 75 µg/ml kanamycin was obtained. The plasmids obtained from the transformant were the same plasmids as those introduced. Where microorganisms of the genus Rhodococcus were used as the host, the presence of IPTG was not required for expression of kanamycin resistance.

Example 3

Construction of Vector for Microorganisms of the Genus Rhodococcus

Figure 3:
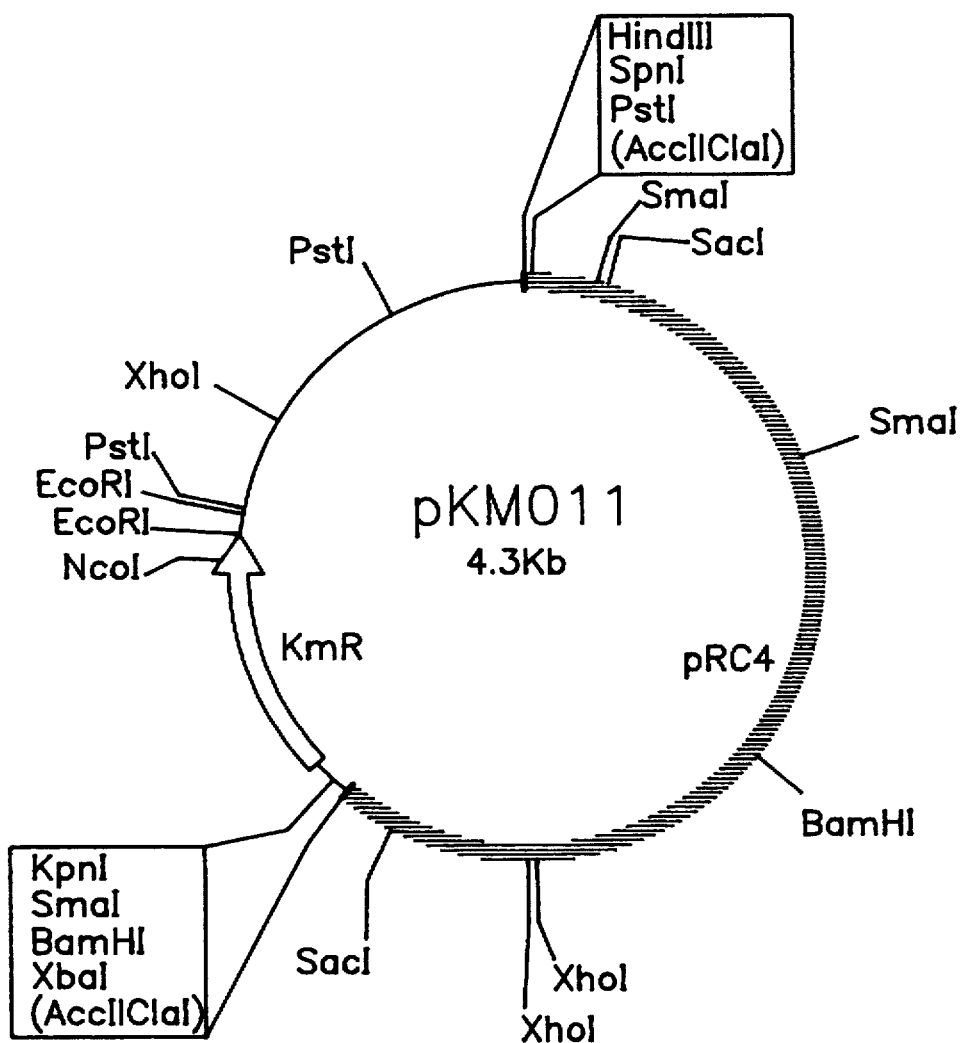
FIG. 3 shows a restriction enzyme map of plasmid pKM011.

The hybrid plasmid vector pKM004 was cleaved with restriction enzyme KpnI to give a 4.3 kb KpnI fragment which was then self-ligated and introduced into *Rhodococcus rhodochrous* ATCC 12674 by electroporation. The resulting transformant showed the same degree of kanamycin resistance as did the transformant of Example 2. From this transformant, a plasmid was obtained and designated pKM011 (FIG. 3).

---

What is claimed is:

1. An isolated DNA molecule which encodes the amino acid sequence of Sequence No. 1.

2. The isolated DNA molecule according to claim 1 having the sequence of SEQ ID NO: 2.

3. The isolated DNA molecule according to claim 1, wherein said DNA molecule is expressed in a host microorganism of the genus Rhodococcus or *Escherichia coli*, wherein said host microorganism is transformed with said DNA molecule.

4. An isolated DNA molecule according to claim 2, wherein said DNA molecule is expressed in a host microorganism of the genus Rhodococcus or *Escherichia coli*, wherein said host microorganism is transformed with said DNA molecule.

5. A plasmid vector comprising a DNA according claim 1 and a DNA region capable of replicating in microorganisms of the genus Rhodococcus.

6. A plasmid vector comprising a DNA according to claim 2 and an isolated DNA region capable of replicating in microorganisms of the genus Rhodococcus.

7. A plasmid vector comprising a DNA according to claim 3 and an isolated DNA region capable of replicating in microorganisms of the genus Rhodococcus.

8. A plasmid vector comprising a DNA according to claim 4 and an isolated DNA region capable of replicating in microorganisms of the genus Rhodococcus.

9. A plasmid vector according to claim 5, wherein the DNA region capable of replicating in microorganisms of the genus Rhodococcus is selected from the group consisting of pRC001, pRC002, pRC003 and pRC004.

10. A plasmid vector according to claim 6, wherein the DNA region capable of replicating in microorganisms of the genus Rhodococcus is derived from a plasmid selected from the group consisting of pRC001, pRC002, pRC003 and pRC004.

11. A plasmid vector according to claim 7, wherein the DNA region capable of replicating in microorganisms of the genus Rhodococcus is selected from the group consisting of pRC001, pRC002, pRC003 and pRC004.

12. A plasmid vector according to claim 8, wherein the DNA region capable of replicating in microorganisms of the genus Rhodococcus is selected from the group consisting of pRC001, pRC002, pRC003 and pRC004.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 144 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Met  Ser  Asp  Asn  Gly  Ser  Gly  Thr  Thr  Arg  Pro  Glu  Gly  Ala  Pro  Leu
1                    5                         10                        15

Pro  Arg  Arg  Ala  Arg  Ser  Ser  Arg  Pro  Ser  Ala  Gly  Asn  Ser  Pro  Ala
               20                        25                        30

Pro  Gly  Arg  Arg  Ala  Val  Val  Ala  Lys  Ser  Arg  Arg  Arg  Leu  Ala  Ala
               35                        40                        45

Ala  Pro  Glu  Ala  Gly  Thr  Thr  His  Tyr  Ser  Ile  Phe  His  Gly  Asp  Gln
     50                        55                        60

Leu  Ile  Gly  Phe  Ile  Gln  Trp  Tyr  Glu  Ala  Glu  Asp  Asn  Pro  Asp  Phe
65                        70                        75                        80

Arg  His  Ala  Gly  Leu  Asp  Leu  Phe  Leu  Asp  Pro  Asp  Phe  His  Gly  Arg
                    85                        90                        95

Gly  Phe  Gly  Arg  Glu  Ser  Ile  Arg  Val  Leu  Cys  Ala  His  Leu  Ile  Asp
                    100                       105                       110

Asp  Leu  Ala  Phe  His  Arg  Leu  Val  Ile  Asp  Pro  Glu  Val  Asp  Asn  Ser
               115                       120                       125

Val  Ala  Ile  Ala  Cys  Tyr  Arg  Ser  Val  Gly  Phe  Lys  Asp  Val  Gly  Val
```

( 2 ) INFORMATION FOR SEQ ID NO:2:

( i ) SEQUENCE CHARACTERISTICS:
        ( A ) LENGTH: 516 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | |
|---|---|---|---|---|---|
| ATGAGTGACA | ACGGCTCCGG | AACTACGCGG | CCCGAGGGTG | CTCCTCTCCC | CCGTCGCGCC | 60 |
| CGATCATCAC | GCCCGTCTGC | GGGCAATTCA | CCTGCACCCG | GACGTCGTGC | AGTGGTGGCA | 120 |
| AAATCCCGAC | GACGACTGGC | TGCGGCGCCA | GAAGCCGGAA | CCACGCACTA | CAGCATCTTC | 180 |
| CACGGCGACC | AACTGATCGG | CTTCATCCAG | TGGTACGAAG | CGGAAGACAA | CCCCGACTTC | 240 |
| CGCCACGCCG | GGCTCGACTT | GTTCCTCGAT | CCCGACTTCC | ACGGCCGAGG | GTTCGGTCGC | 300 |
| GAATCGATTC | GCGTGCTGTG | TGCCCACCTG | ATCGACGACC | TCGCATTCCA | CCGTCTGGTC | 360 |
| ATCGACCCGG | AGGTCGACAA | CTCCGTCGCC | ATCGCGTGCT | ACCGATCGGT | GGGGTTCAAA | 420 |
| GACGTCGGGG | TGATGCGCGA | GTATTCGCGA | GATCGCCATG | GTGTGTGGAA | GGACGGACTG | 480 |
| CTGATGGATC | TGCTCGCACG | GGAATTCATC | CGCTGA | | | 516 |

( 2 ) INFORMATION FOR SEQ ID NO:3:

( i ) SEQUENCE CHARACTERISTICS:
        ( A ) LENGTH: 748 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

| | | | | | |
|---|---|---|---|---|---|
| GGATCCGGGG | TCGTCGCCCA | CCAGGATGGT | ACCCAAGCCG | GGTGTGATGC | CCTCTGCCTT | 60 |
| CGAGCGCTCA | CCCGCACCTT | CAGGTCTTCG | AAGATTTCGT | CGCGGGTAGC | TTTGCCGTCG | 120 |
| AGGATCGTTG | CAGTCACGGC | GACCATTGTT | CCAGGTTAGG | GTCGATGAGT | GACAACGGCT | 180 |
| CCGGAACTAC | GCGGCCCGAG | GGTGCTCCTC | TCCCCCGTCG | CGCCCGATCA | TCACGCCCGT | 240 |
| CTGCGGGCAA | TTCACCTGCA | CCCGGACGTC | GTGCAGTCGT | GGCAAAATCC | CGACGACGAC | 300 |
| TGGCTGCGGC | GCCAGAAGCC | GGAACCACGC | ACTACAGCAT | CTTCCACGGC | GACCAACTGA | 360 |
| TCGGCTTCAT | CCAGTGGTAC | GAAGCGGAAG | ACAACCCCGA | CTTCCGCCAC | GCCGGGCTCG | 420 |
| ACTTGTTCCT | CGATCCCGAC | TTCCACGGCC | GAGGGTTCGG | TCGCGAATCG | ATTCGCGTGC | 480 |
| TGTGTGCCCA | CCTGATCGAC | GACCTCGCAT | CCACCGTCT | GGTCATCGAC | CCGGAGGTCG | 540 |
| ACAACTCCGT | CGCCATCGCG | TGCTACCGAT | CGGTGGGGTT | CAAAGACGTC | GGGGTGATGC | 600 |
| GCGAGTATTC | GCGAGATCGC | CATGGTGTGT | GGAAGGACGG | ACTGCTGATG | GATCTGCTCG | 660 |
| CACGGGAATT | CATCCGCTGA | TCGACTGGGA | CGAGTTCGAA | AGGACCGACA | TCATGTTGCT | 720 |
| GGACAAGGAA | TTCACGGCCA | CCCTGCAG | | | | 748 |